(12) United States Patent
To et al.

(10) Patent No.: US 9,273,229 B2
(45) Date of Patent: Mar. 1, 2016

(54) METHOD FOR DE-COLORING SHELLAC, DE-COLORED SHELLAC, COMPOSITIONS COMPRISING SAME, AND USES THEREFOR

(71) Applicant: d-ANTAEUS, Montreal, Quebec (CA)

(72) Inventors: Thi Cong To, Quebec (CA); Thuc Soan Nguyen, Quebec (CA)

(73) Assignee: d-ANTAEUS, Montreal (CA)

( * ) Notice: Subject to any disclaimer, the term of this patent is extended or adjusted under 35 U.S.C. 154(b) by 218 days.

(21) Appl. No.: 13/942,331

(22) Filed: Jul. 15, 2013

(65) Prior Publication Data

US 2014/0065079 A1    Mar. 6, 2014

Related U.S. Application Data

(60) Provisional application No. 61/696,851, filed on Sep. 5, 2012.

(51) Int. Cl.
| | |
|---|---|
| *C09F 1/00* | (2006.01) |
| *A61Q 11/00* | (2006.01) |
| *C09F 1/02* | (2006.01) |
| *A61K 6/00* | (2006.01) |
| *A61Q 3/02* | (2006.01) |
| *A61K 8/98* | (2006.01) |

(52) U.S. Cl.
CPC ............. *C09F 1/00* (2013.01); *A61K 6/0058* (2013.01); *A61K 8/987* (2013.01); *A61Q 3/02* (2013.01); *A61Q 11/00* (2013.01); *C09F 1/02* (2013.01); *A61K 2800/805* (2013.01)

(58) Field of Classification Search
USPC ............................ 424/52, 451, 481; 530/201
See application file for complete search history.

(56) References Cited

U.S. PATENT DOCUMENTS

| | | | | |
|---|---|---|---|---|
| 2,397,389 | A  * | 3/1946 | Vincent .......................... | 530/201 |
| 6,348,217 | B1 * | 2/2002 | Santos et al. .................. | 424/481 |
| 6,620,431 | B1 * | 9/2003 | Signorino ...................... | 424/451 |
| 2011/0033394 | A1 * | 2/2011 | Blanvalet et al. ............... | 424/52 |

OTHER PUBLICATIONS

Sharma, S. K. et al. Shellac—Structure, Characteristics & Modification. Def Sci J. vol. 33, No. 3, Jul. 1983, pp. 261-271.
Phuong Ha, Huynh Ky et al. Chemical Bleaching on Shellac. KMU-HCMUT Joint Workshop. Jan 2008, p. 55.

* cited by examiner

*Primary Examiner* — Walter Webb
(74) *Attorney, Agent, or Firm* — Banner & Witcoff, Ltd.

(57) ABSTRACT

A method for producing de-colored shellac by dissolving colored shellac in an aqueous solution comprising an alkaline agent; contacting the colored shellac in the aqueous solution with a sufficient amount of a chlorite salt to achieve de-coloration of the shellac; precipitating the de-colored shellac by neutralizing the aqueous solution with an acid; and recovering the precipitated de-colored shellac from said aqueous solution. The de-colored shellac produced is non-toxic and suitable for human use. Dental compositions comprising the de-colored shellac are disclosed, as well as uses of the de-colored shellac as a food product coating, a nail polish or varnish, and a wood varnish.

16 Claims, 2 Drawing Sheets

METHOD FOR DE-COLORING SHELLAC, DE-COLORED SHELLAC, COMPOSITIONS COMPRISING SAME, AND USES THEREFOR

CROSS REFERENCE TO RELATED APPLICATIONS

This application claims benefit, under 35 U.S.C. §119(e), of U.S. Provisional Application Ser. No. 61/696,851, filed on Sep. 5, 2012. All documents above are incorporated herein in their entirety by reference.

FIELD OF THE INVENTION

The present invention relates to a method of removing, completely or partially, the natural residual color from raw or processed shellac to produce de-colored shellac. More particularly, the present invention relates to uses of de-colored shellac for example in dental compositions.

BACKGROUND OF THE INVENTION

Shellac is a natural, non-toxic resin secreted on the barks of trees by the female lac insect (*Kerria lacca*). Raw shellac can be collected, processed and sold as dry flakes, which can then be dissolved in a solvent to make liquid shellac. Shellac comes in many colors and its color is influenced by the sap of the tree the lac insect is living on, as well as the time of harvest. Raw, unprocessed shellac is normally orange to brown in color.

Raw shellac is a mixture of many molecules and can be separated into three main components: (1) hard resin; (2) soft resin; and (3) wax. Raw shellac can be processed to remove the wax and can also be bleached. Traditional bleaching techniques fail to produce shellac that is truly colorless or more de-colored, and a significant amount of color remains. Some manufacturers market their bleached shellac as "white", but a closer examination of their product reveals that it is in fact pale yellow and not purely white. The presence of this residual color in the shellac resin is unsuitable for a number of applications in which clear and colorless or more de-colored shellac is desired, or the presence of residual color would be aesthetically or cosmetically unappealing.

One industry which would welcome colorless shellac or a more de-colored product is the dental industry. Dental decay affects the majority of the population and poses a serious and sometimes expensive problem, particularly for young children. A shellac-based dental coating product would be welcomed, yet the presence of residual color in the shellac resin renders such a product cosmetically unappealing for certain cultures where, for example, whiter teeth is considered attractive. Furthermore, more durable shellac-based dental coating products, which can withstand regular abuse such as eating, drinking and brushing, would also be desirable.

Another industry which would welcome colorless shellac or a more de-colored product is the food and drug industry. Shellac is edible and it is used as a glazing agent on pills and candies in the form of pharmaceutical glaze (or confectioner's glaze). Shellac is also suitable as a food coating, and has been used to replace the natural wax of apples, which is removed during the cleaning process. A colorless or a more de-colored shellac product may be more aesthetically appealing. Other industries would also welcome colorless or more de-colored shellac products. For example, shellac is an odor and stain blocker and can be used as a primer for a variety of surfaces to provide, for example, a barrier against water. Shellac is also used in nail varnishes and nail polishes, and colorless or more de-colored shellac may be desirable in such products.

The present description refers to a number of documents, the content of which is herein incorporated by reference in their entirety.

SUMMARY OF THE INVENTION

The present invention relates to the discovery of a method for removing, either completely or partially, the residual color (e.g., residual yellow or orange color) from conventionally processed shellac, in order to produce colorless shellac or more de-colored shellac.

More particularly, methods of de-coloring shellac according to the present invention generally include the following main steps: Dissolution of the colored shellac used as starting material using an alkaline agent; de-colorization/bleaching of the dissolved colored shellac using a bleaching agent; precipitation/recovery of the de-colored shellac using a neutralization agent; rinsing and drying of the de-colored shellac.

Accordingly, in one aspect, the present invention relates to a method for de-coloring shellac, the method comprising:
(a) heating and dissolving colored shellac in an aqueous solution comprising an alkaline agent;
(b) contacting the colored shellac in the aqueous solution with a sufficient amount of a chlorite salt to de-color the colored shellac;
(c) precipitating the de-colored shellac by neutralizing the aqueous solution in (b) with an acid; and
(d) recovering the precipitated de-colored shellac from the aqueous solution, thereby de-coloring the colored shellac.

In one embodiment, the colored shellac mentioned above has been previously bleached with a bleaching agent other than the chlorite salt.

In another embodiment, the above-mentioned method further comprises (e) drying the de-colored shellac. In another embodiment, the drying occurs at a temperature of about 40° C. or less, or by freeze drying.

In another embodiment, the above-mentioned aqueous solution does not comprise an organic chemical solvent. In another embodiment, the above-mentioned aqueous solution does not comprise an alcohol. In another embodiment, the above-mentioned aqueous solution does not comprise ethanol.

In another embodiment, the above-mentioned alkaline agent is a weak base. In another embodiment, the above-mentioned alkaline agent is a bicarbonate salt. In another embodiment, the above-mentioned bicarbonate salt is sodium bicarbonate ($NaHCO_3$).

In another embodiment, the above-mentioned chlorite salt is sodium chlorite ($NaClO_2$). In another embodiment, the above-mentioned sufficient amount of the chlorite salt is about 5-20% wt/wt of the shellac.

In another embodiment, the above-mentioned acid is: acetic acid ($CH_3COOH$), hydrochloric acid (HCl) or sulfuric acid ($H_2SO_4$). In another embodiment, the above-mentioned acid is acetic acid ($CH_3COOH$).

In another embodiment, the above-mentioned recovering step in (d) is via filtration, or centrifugation.

In another embodiment, the above-mentioned the de-colored shellac is colorless shellac.

In another aspect, the present invention relates to a method of producing a de-colored shellac composition comprising the any one of the methods mentioned above, further comprising adding an additive during and/or after (a), (b), (c), and/or (d), wherein the additive is selected from: an organic additive; metallic oxide nanoparticles; an anti-caries agent; a flavor or odor improving agent; and any combination thereof.

In one embodiment, the above-mentioned additive is added during (a). In another embodiment, the above-mentioned additive added after (d) is added during or after re-dissolution of the de-colored shellac.

In another embodiment, the above-mentioned additive is dispersed by mixing and/or using an ultrasound device.

In another embodiment, the above-mentioned organic additive is an organic dispersant or stabilizing agent selected from: a polymer at low molecular weight, polyacrylate or polyacrylic acid sodium salt (PAA), polyethylene glycol (PEG), polypropylene glycol (PPG), polyepoxysuccinic acid (PES-A) or sodium salt thereof (PES-Na), poly(itaconic) acid, cellulose derivative such as carboxymethyl cellulose (CMC), sulfonated carboxylic acid terpolymer, a copolymer of acrylic acid and sulfonated monomers thereof (Co-PAA); or any combination thereof.

In another embodiment, the above-mentioned additive is a small molecule having multifunctional groups selected from: 2-phosphonobutane-1,2,4 tricarboxylic acid (DEQUEST™ 7000); sodium hexametaphosphate (HMP); and any combination thereof.

In another embodiment, the above-mentioned metallic oxide nanoparticles have an average size less than or equal to 75 nm. In another embodiment, aggregates of the above-mentioned metallic oxide nanoparticles have an average size less than or equal to 100 nm±20 nm. In another embodiment, the above-mentioned metallic oxide nanoparticles have an average size between about 5 nm and 30 nm.

In another embodiment, the above-mentioned metallic oxide nanoparticle is an oxide of Ti, Zn, Mg, Si, Al, Ce, Fe, or any combination thereof. In another embodiment, the above-mentioned metallic oxide nanoparticle is selected from: titanium oxide; zinc oxide; magnesium oxide, silicium oxide, aluminum oxide; and any combination thereof.

In another embodiment, the above-mentioned the anti-caries agent is selected from: sodium fluoride; sodium fluorophosphate; and stannous fluoride.

In another embodiment, the above-mentioned flavor or odor improving agent is an essential oil.

In another aspect, the present invention relates to a de-colored shellac produced according to any one of the above mentioned methods.

In another aspect, the present invention relates to a composition (i) produced by any one of the above mentioned methods, or (ii) comprising the de-colored shellac as defined above, and a suitable carrier.

In one embodiment, the above mentioned carrier is a non-toxic, volatile solvent. In another embodiment, the above mentioned carrier is ethanol. In another embodiment, the concentration of de-colored shellac/ethanol is about 1 to about 40%, preferably about 15 to about 40% (w/w).

In another embodiment, the above-mentioned de-colored shellac is present in an amount of about 5% to about 40% (wt/wt) based on the weight of the composition. In another embodiment, the above mentioned de-colored shellac in present in an amount of about 5% to about 30% (wt/wt) based on the weight of the composition. In another embodiment, the above mentioned de-colored shellac is present in an amount of about 10% to about 20% (wt/wt) based on the weight of the composition. In another embodiment, the above mentioned the de-colored shellac is present in an amount of about 15% to about 40% (wt/wt) based on the weight of the composition.

In another embodiment, the above mentioned metallic oxide nanoparticles are present in an amount of about 0.05% to about 5% (wt/wt) based on the weight of the composition.

In another embodiment, the above mentioned metallic oxide nanoparticles are present in an amount of about 0.05% to about 2% (wt/wt) based on the weight of the composition.

In another embodiment, the above mentioned organic dispersant or stabilizing agent is present in an amount of about 0.05% to 5% (wt/wt) based on the weight of the composition. In another embodiment, the above mentioned organic dispersant or stabilizing agent is present in an amount of about 0.05% to 2% (wt/wt) based on the weight of the composition.

In another embodiment, the above mentioned composition is for use as a dental composition. In another embodiment, the above mentioned dental composition is substantially resistant to regular brushing for at least 3 months.

In another aspect, the present invention relates to a method for:
  (i) protecting tooth enamel from dental caries, dental decay, and/or acids;
  (ii) preventing or treating dentinal hypersensitivity; and/or
  (iii) improving the cosmetic appearance of teeth;
the method comprising:
  (a) dissolving the composition of claim 43, in ethanol to produce a shellac-ethanol solution;
  (b) applying the shellac-ethanol solution to a tooth; and
  (c) drying the solution.

In one embodiment, the above mentioned method further comprises applying shellac-ethanol solutions in multiple successive coats or mixing different shellac-ethanol solutions prior to application to the tooth. In another embodiment, the shellac-ethanol solutions can be applied in successive coats, or the different shellac-ethanol solutions that are mixed have different colors and/or additives.

In another aspect, the present invention relates to the use of:
  (1) the de-colored shellac produced by any one of the above mentioned methods;
  (2) the composition produced by any one of the above mentioned methods; or
  (3) the composition as defined above,
for applying to a tooth, or for the manufacture of a product for application to a tooth.

In another aspect, the present invention relates to a composition comprising the de-colored shellac produced by any one of the methods mentioned above and a suitable carrier, wherein the composition is for use as: a coating for a food product; an art material; a nail varnish or polish; or a wood varnish.

In another aspect, the present invention relates to the use of the de-colored shellac produced by any one of the methods mentioned above as a food product coating, as an art material, as a nail varnish or polish, as a wood varnish; or for the manufacture of a product for accomplishing same.

In another aspect, the present invention relates to a kit comprising
  (1) the de-colored shellac produced by any one of the above mentioned methods;
  (2) the composition produced by any one of the above mentioned methods; or
  (3) the composition as defined above,
and a suitable container.

In one embodiment, the above mentioned kit further comprises a colored shellac composition for obtaining a range of possible desired final colors.

Other objects, advantages and features of the present invention will become more apparent upon reading of the following non-restrictive description of specific embodiments thereof.

DESCRIPTION OF ILLUSTRATIVE EMBODIMENTS

Definitions

Figure 1:
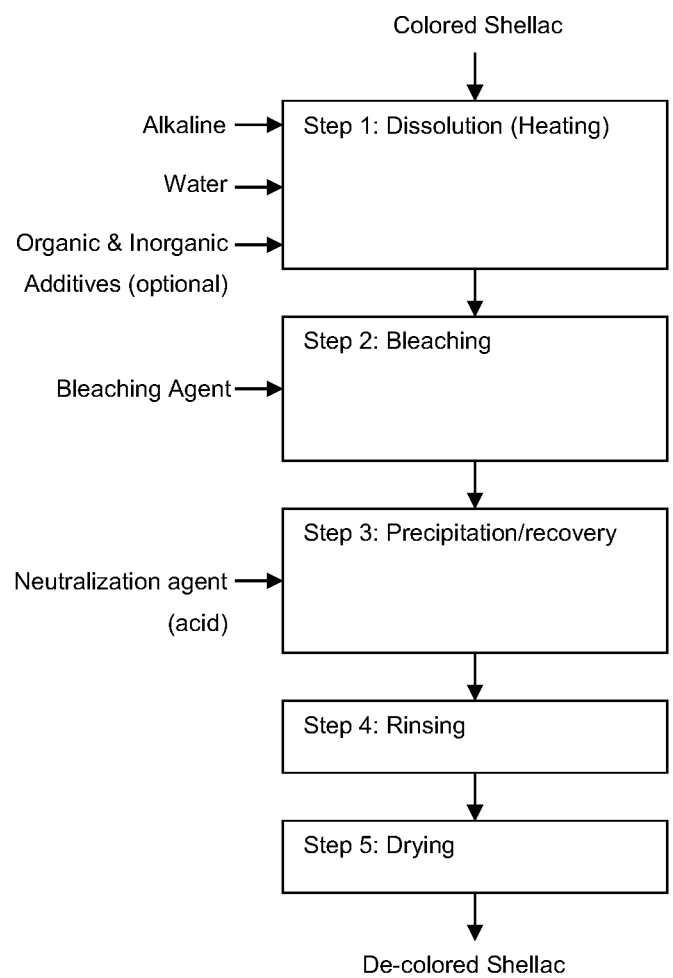
FIG. 1 is a schematic diagram of a method for de-coloring shellac according to one embodiment of the present invention, which involves five main steps: Dissolution; Bleaching; Precipitation/recovery; Rinsing and Drying.

In the present description, a number of terms are extensively utilized. In order to provide a clear and consistent understanding of the specification and claims, including the scope to be given to such terms, the following definitions are provided.

Unless defined otherwise, the scientific and technological terms and nomenclature used herein have the same meaning as commonly understood by a person of ordinary skill in the art to which this invention pertains.

The use of the word "a" or "an" when used in conjunction with the term "comprising" in the claims and/or the specification may mean "one" but it is also consistent with the meaning of "one or more", "at least one", and "one or more than one".

Throughout this application, the term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about".

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "subject", "patient" or "user" as used herein refers to an animal, preferably a mammal, and most preferably a human who is the subject of treatment, observation or experiment.

As used herein, the term "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by regulatory agency of the federal or state government or listed in the U.S. Pharmacopeia or other generally recognized pharmacopeia for use in animals, and more particularly in humans. The term "carrier" refers to a diluent, excipient, or vehicle with which the compounds of the present invention may be used or administered. Sterile water or aqueous saline solutions may be employed as carrier. Suitable pharmaceutical carriers are described in "Remington's Pharmaceutical Sciences" by E. W. Martin.

As used herein, the terms "shellac" or "lac" relate to the resinous secretions of a number of species of insects, namely some of the species of the genera *Metatachardia, Laccifer, Tachordiella, Austrotacharidia, Afrotachardina*, and *Tachardina* of the superfamily Coccoidea, of which the most commonly cultivated species is *Kerria lacca*. The terms "shellac" and "lac" include raw shellac, processed shellac, and purified shellac. By "raw shellac", it is meant shellac that has been collected but has not been de-waxed and/or bleached. By "processed shellac" it is meant shellac that has been collected and processed, for example, to be de-waxed, bleached, or purified.

As used herein, "colored shellac" refers to raw or processed shellac which possesses a sufficient amount residual natural shellac color that is visible to the unaided eye. The amount of residual color present in the colored shellac can vary to produce shellac that is anywhere from pale yellow or beige to dark orange, red or brown.

As used herein, "de-colored shellac" or "de-pigmented shellac" refers to any raw or processed shellac that has been subjected to the methods of the present invention in order to remove, either completely or partially, natural remaining or natural residual visible color from the shellac in order to produce a shellac product that, when dried, visually appears more devoid of color (i.e., more de-colored/de-pigmented, or more white/"whiter") than the colored shellac used as the starting material. For example, shellac subjected to the methods of the present invention may have a reduced level of color (or increased whiteness), when dried, due to the removal of residual yellow (or other) color.

As used herein, "colorless shellac" refers to a shellac product subjected to the methods of the present invention which is substantially colorless when dried. The residual color that is removed from the colored shellac can be light or faint (e.g., pale yellow) or dark (e.g., orange, red or brown), or any shade there between. As used herein, the term "colorless", when used in the phrase "colorless shellac" includes shellac that is substantially clear, transparent (e.g., in solution), white (including variations thereof; in solid or solution phases), or opaquely white; but excludes shellac that is yellow, orange, red, brown, grey, black and all shades in between. As used herein, the term "colorless" is encompassed by the term "de-colored".

A "natural product" refers to any product (e.g., shellac) that may be produced by, found in, or extracted from a living organism, such as, for example, an animal or a plant. An "all-natural product" refers to a product made with and/or from only natural compounds or products.

"Generally recognized as safe" or "GRAS" refers to an American Food and Drug Administration (FDA) designation that a chemical or substance added to food is considered safe by experts, and may be exempted from some other regulatory requirements. These substances can be referred to as "qualifying for a GRAS exemption" or "GRAS exempted".

An "organic chemical solvent" refers to any solvent containing at least one carbon atom.

Shellac Suitable as Starting Material

Raw shellac resin consists of many different compounds. Raw shellac can be fractioned into three main components namely hard resin, soft resin and wax (Sharma et al., 1983). The hard resin includes compounds such as aleuritic acid, jalaric acid and laccijalaric acid. The soft resin includes a mixture of dyes such as erythrolaccin and desoxyerythrolaccin, which is the source of the natural color (e.g., bright orange to reddish brown color) in raw, unbleached shellac.

The present invention relates to a method for de-coloring raw shellac that has been previously processed (e.g., bleached and de-waxed), but which still retains some of its natural color. Bleaching agents that are routinely used in the shellac processing industry include: sodium hypochlorite (NaOCl); hydrogen peroxide ($H_2O_2$); ozone ($O_3$); chlorine dioxide ($ClO_2$); and potassium permanganate ($KMnO_4$). Shellac manufacturers typically collect and process raw shellac and sell it, for example, as dry flakes in a variety of colors. These colors can range from light yellow (e.g., "blond" or "platina") to a very dark brown (e.g., "garnet"), including different shades of brown, yellow, orange and red in between. Such colors are also excluded from the expression "colorless shellac" as used herein. However, truly colorless shellac (e.g., transparent, or white when dissolved in a solvent such as ethanol) shellac per se has been traditionally elusive.

The shellac that can be used as starting material in accordance with the present invention includes processed raw shellac as discussed above. As used herein, "processed colored shellac" or simply "colored shellac" refers to any processed form (e.g., liquid or solid) of raw shellac which has been de-waxed and bleached, which still retains some of its natural residual color, and which is suitable as a starting material for the methods of the present invention. Raw shellac is generally subjected to de-waxing in order to increase its solubility, and the level of residual wax in a given shellac sample can be determined empirically, for example, by measuring its solubility in an alkaline solution. Accordingly, the level of de-waxing of the shellac used as starting material is such that it allows the shellac to be dissolved in an aqueous solution comprising an alkaline agent (e.g., bicarbonate) in accordance with the methods of the present invention.

Because the color of raw shellac may be influenced by a number of factors such as the tree the lac insect is living on and the time of harvest, raw shellac originating from different geographic locations (or harvested at different times of year) may yield raw shellac having different colors. Furthermore, shellac processing companies may offer additional colors of shellac produced by varying their processing methods (e.g., degree of bleaching). Accordingly, the geographic origin and/or the color of the processed shellac may be taken into account when selecting the colored shellac to be used as starting material in accordance with the present invention. In an embodiment, the colored shellac used as starting material is derived from raw shellac harvested and purified from Asia (e.g., "white de-waxed shellac" from India (e.g., article number 60450, CAS 9000-59-3; EINECS 232-549-9)). In other embodiments, the shellac used as starting material is derived from Thailand. In another embodiment, the shellac use the starting material is "blonde" shellac.

Schema of De-colored Process

As shown schematically in FIG. 1, methods of de-coloring shellac according to the present invention generally include the following main steps: Dissolution of the colored shellac used as starting material using an alkaline agent; de-colorization/bleaching of the dissolved colored shellac using a bleaching agent; precipitation/recovery of the de-colored shellac using a neutralization agent; rinsing and drying of the de-colored shellac.

Dissolution of Colored Shellac

In accordance with the present invention, the colored shellac is dissolved in an aqueous solution comprising an alkaline agent. More particularly, the composition of the aqueous solution should allow the dissolution of both the colored shellac used as starting material, and the bleaching agent that is selected. In one embodiment, the aqueous solution does not comprise an organic chemical solvent. In another embodiment, the aqueous solution does not comprise an alcohol (e.g., ethanol). In another embodiment, the aqueous solution does not comprise a compound present in an amount that does not qualify for a GRAS exemption.

By "alkaline agent", it is meant one or more compounds that can raise the pH of water sufficiently to allow the dissolution of the colored shellac. In one embodiment, the alkaline agent includes a mixture of different alkaline agents. In another embodiment, the alkaline agent includes a weak alkaline agent such as a weak base. In another embodiment, the weak alkaline agent is a bicarbonate salt. In another embodiment, the bicarbonate salt is sodium bicarbonate ($NaHCO_3$). In another embodiment, the alkaline agent is a compound which qualifies for a GRAS exemption.

The amount or concentration of the alkaline agent to be used in accordance with the present invention is an amount or concentration which allows sufficient dissolution of the colored shellac used as starting material. In one embodiment, the amount of the alkaline agent (e.g., sodium bicarbonate) is about 1 g to 8 g per 10 g of colored shellac used as starting material.

In one embodiment, the aqueous solution comprising the colored shellac can be heated to aid in dissolution. In another embodiment, the aqueous solution comprising the colored shellac can be heated to the minimum temperature sufficient to result in dissolution of the shellac used as starting material. In another embodiment, the aqueous solution comprising the colored shellac can be heated to approximately the melting point of the shellac (e.g., about 70 to about 90° C.). In another embodiment, the aqueous solution comprising the colored shellac can be heated to about 80° C. In another embodiment, the aqueous solution comprising the colored shellac can be heated to about 40° C., about 50° C., about 60° C., about 70° C., about 80° C., or about 90° C. In another embodiment, the aqueous solution comprising the colored shellac can be heated to a temperature not greater than about 80° C. or about 90° C. In another embodiment, the heating time can be between about 5 minutes to about 30 minutes. In another embodiment, the heating time can be between about 25 minutes.

In another embodiment, the aqueous solution comprising the shellac is mixed to further aid in dissolution. The duration of time for heating, mixing, or dissolution depends on the source and/or purity of the colored shellac used as starting material.

De-colorization/Bleaching of Colored Shellac

In accordance with the present invention, the colored shellac dissolved in said aqueous solution is contacted with a sufficient amount of a bleaching agent to remove, either completely or partially, remaining color from the colored shellac used as starting material.

By "bleaching agent", it is meant an oxidizing agent capable of reacting with the colored shellac to remove, either completely or partially, natural remaining or natural residual visible color from the shellac in order to produce a de-colored, de-pigmented or whiter shellac product that, when dried, visually appears more devoid of color (i.e., more de-colored, more de-pigmented, more white/"whiter") than the shellac used as the starting material. In another embodiment, the amount of the bleaching agent used can be adapted according to the amount of color present in the colored shellac used as starting material. Bleaching agents that are routinely used in the shellac processing industry include: sodium hypochlorite (NaOCl); hydrogen peroxide ($H_2O_2$); ozone ($O_3$); chlorine dioxide ($ClO_2$); and potassium permanganate ($KMnO_4$).

In one embodiment, the bleaching agent can include a chlorite salt or a metal chlorite. In another embodiment, the bleaching agent can include sodium chlorite ($NaClO_2$). In another embodiment, the amount of chlorite salt (e.g., sodium chlorite) used can be between about 0.5 g and about 4 g per 10 g of colored shellac used as starting material. In another embodiment, the amount of chlorite salt (e.g., sodium chlorite) used can be between about 5-20% (wt/wt) of colored shellac used as starting material. In another embodiment, the amount of chlorite salt (e.g., sodium chlorite) used can be adapted according to the amount of color present in the colored shellac used as starting material.

Precipitation and Recovery of De-colored Shellac

In accordance with the present invention, the de-colored shellac can be precipitated from the alkaline aqueous solution by neutralizing the solution with an acid. By "neutralizing" it is meant lowering the pH of the alkaline aqueous solution to sufficiently precipitate and allow recovery of the de-colored shellac. In one embodiment, the pH of the alkaline aqueous solution can be lowered to about pH 6 to about pH 7. In another embodiment, the pH of the alkaline aqueous solution can be lowered to about pH 7.

In one embodiment, the acid used for precipitation includes a weak acid such as acetic acid ($CH_3COOH$). In another embodiment, the concentration of the weak acid is about 20% (w/w). In another embodiment, the acid used for precipitation includes a strong acid such as hydrochloric acid (HCl) or sulfuric acid ($H_2SO_4$). In another embodiment, the acid used for precipitation includes a mixture of a strong acid and a weak acid.

The precipitated de-colored shellac can be recovered, for example, by filtering and/or by centrifugation. In one embodiment, the precipitated de-colored shellac is washed (e.g., with water) after precipitation, for example, to remove salts formed during the reaction. In another embodiment, the precipitated de-colored shellac is dried, for example, at a maximum temperature of 40° C. In another embodiment, the drying can be performed at room temperature. In another embodiment, the drying can be performed by freeze-drying.

In accordance with the present invention, the de-colored shellac that has been recovered and dried as described above can be dissolved in a suitable solvent such as ethanol. Such a solvent evaporates relatively quickly after application of the composition on a surface and results in a layer of shellac that is substantially transparent. In an embodiment, the concentration of shellac/ethanol is about 1% to about 40%, preferably about 15% to about 40% (w/w).

Addition of Additives

Figure 2:
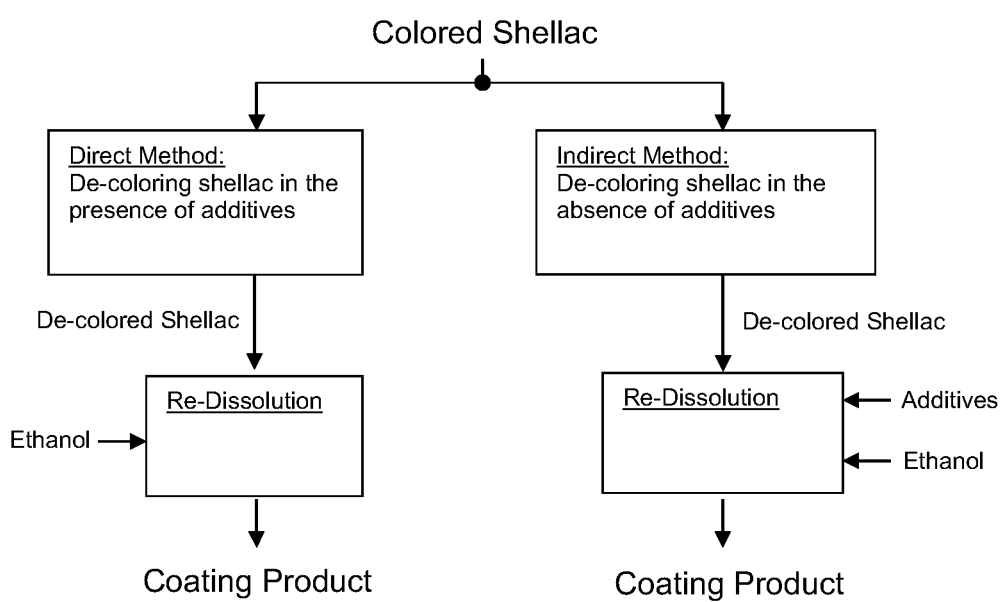
FIG. 2 is a schematic diagram representing different methods (direct and indirect) for adding additives to the de-colored shellac according to two embodiments of the present invention. In the direct method, additives are mixed in at the beginning. In the indirect method, the primary shellac de-coloring does not involve the addition of additives, but the additives may be added at the final re-dissolution step. In another embodiment, the direct and indirect methods can be combined and additives may be added both at the beginning and at the end.

A variety of different additives can be optionally added during or after any step in the shellac de-colorization process of the present invention. For example, as shown schematically in FIG. 2, the additives can be mixed at the beginning ("direct method") or at the end during the re-dissolution step ("indirect method") of the de-coloration process. In an embodiment, the direct and indirect methods can be combined and additives may be added both at the beginning and at the end.

As used herein, "additive" or "filler" refers to a substance, or a combination of different substances, added in relatively small amounts to improve, modify, and/or impart an additional desirable functionality or characteristic to raw shellac, colored shellac, or the de-colored shellac of the present invention. Examples of such functionalities or characteristics include hardness, durability, color, protective ability, adherence properties, and applicability.

In another embodiment, the additive includes an organic additive. As used herein, "organic additive" refers to an additive as defined above whose molecules include carbon. In another embodiment, the organic additive includes an organic dispersant or stabilizing agent such as such as a polymer at low molecular weight, polyacrylate or polyacrylic acid sodium salt (PAA; e.g., PAA 2100), polyethylene glycol (PEG; e.g., PEG 400, PEG 2000, PEG 4600), polypropylene glycol (PPG; e.g., PPG 1000), polyepoxysuccinic acid (PES-A) or sodium salt thereof (PES-Na), poly(itaconic) acid, cellulose derivative such as carboxymethyl cellulose (CMC), sulfonated carboxylic acid terpolymer (BECLENE™ 400), a copolymer of acrylic acid and sulfonated monomers thereof (Co-PAA; AQUTREAT™ AR540); or any combination thereof. In other embodiments, the additives include small molecules having multifunctional groups e.g. DEQUEST™ 7000 (2-Phosphonobutane-1,2,4 tricarboxylic acid); Sodium Hexametaphosphate (HMP) or any combination thereof.

In another embodiment, the additive includes a metallic oxide nanoparticle. As used here, "nanoparticles" or "NP", refers generally to particles having an average size of less than or equal to 100 nm±20 nm. In another embodiment, metallic oxide nanoparticles of the present invention include an oxide of a metal such as Ti, Al, Zn, Ce, Fe, Mg, Si, or any combination thereof. More particularly, metallic oxide nanoparticles of the present invention include titan white (titanium oxide), titan black, zinc oxide, red iron oxide, chromium oxide, black iron oxide, cobalt blue, alumina white, yellow iron oxide, veridian, zinc sulfide, lithopone, cadmium yellow, vermilion, cadmium red, chrome yellow, molybdade orange, zinc chromate, strontium chromate, white carbon, ultramarine blue, lead white, Prussian blue, mangan violet, aluminum powder, and brass powder, organic pigments such as C. I. 16185, C. I. 45430, C. I. 16255, C. I. 45410, C. I. 45440, C. I. 45100, C. I. 19140, C. I. 15985, C. I. 42053, C. I. 42090, C. I. 73015, C. I. 15850, C. I. 15585, C. I. 15630, C. I. 45170, C. I. 15800, C. I. 15880, C. I. 12120, C. I. 45380, C. I. 26100, C. I. 73360, C. I. 17200, C. I. 12085, C. I. 45370, C. I. 12075, C. I. 21110, C. I. 15510, C. I. 45425, C. I. 45350, C. I. 47005, C. I. 47000, C. I. 21090, C. I. 61570, C. I. 61565, C. I. 59040, C. I. 42095, C. I. 73000, C. I. 42052, C. I. 69825, C. I. 42090, C. I. 20170, C. I. 60725, C. I. 45190, C. I. 15865, C. I. 26105, C. I. 16155, C. I. 16150, C. I. 14700, C. I. 12140, C. I. 15620, C. I. 11725, C. I. 14600, C. I. 12100, C. I. 11680, C. I. 18950, C. I. 10316, C. I. 11380, C. I. 11390, C. I. 13065, C. I. 18820, C. I. 10020, C. I. 42085, C. I. 61520, C. I. 74160, C. I. 60730, and C. I. 20470, and lake pigments which are acid dyes.

In another embodiment, metallic oxide nanoparticles of the present invention include titanium oxide ($TiO_2$), aluminum oxide, zinc oxide, silicium oxide, and/or any combination thereof. In another embodiment, metallic oxide nanoparticles of the present invention have an average size of less than or equal to 100 nm±20 nm. In another embodiment, metallic oxide nanoparticles of the present invention have an average size of less than or equal to 60 nm. In another embodiment, metallic oxide nanoparticles of the present invention have an average size of between about 5 nm and about 30 nm. In another embodiment, metallic oxide nanoparticles of the present invention have an average size of between about 15 nm and about 75 nm. In general, nanoparticles naturally aggregate together to form larger particles. In an embodiment, at least one dispersant is used to limit aggregation by covering each nanoparticle's surface.

In another embodiment, the additive includes a flavor or odor improving agent such as an essential oil. In another embodiment, the additive includes a luminescence agent.

In another embodiment, the additive includes any combination of the additives mentioned above.

De-colored Shellac Compositions

The present invention relates to de-colored shellac produced by the methods presently described, as well as compositions including same. In embodiments, the compositions include de-colored shellac in an amount of about 5% to about 40% (wt/wt), about 5% to about 30% (wt/wt), about 10% to about 42% (wt/wt) or about 15% to about 40% (wt/wt) based on the weight of the composition.

In one embodiment, the compositions of the present invention can include an organic dispersant and/or stabilizing agent in an amount of 0% to about 10% (wt/wt), about 0.05% to about 5% (wt/wt), about 0.05% to about 2% (wt/wt) based on the weight of the composition.

In another embodiment, the compositions of the present invention can include metallic oxide nanoparticles in an amount of 0.05% to about 5% (wt/wt), or 0.05% to about 2% (wt/wt) based on the weight of the composition.

In another embodiment, the de-colored shellac compositions of the present invention relate to safe natural products. In another embodiment, the de-colored shellac compositions of the present invention possess one or more of the following properties: seal out moisture; low hygroscopic properties; low thermal conductivity (i.e., acts as an insulator); excellent adhesion to a wide variety of surfaces; can produce a film of substantial hardness, shine and strength; hypoallergenic; biologically degradable; and resistance to UV rays.

Dental Compositions

In another aspect, the present invention relates to a dental composition including the de-colored shellac of the present invention. As used herein, a "dental composition" may include dental coatings/veneers, and dental restorative materials (e.g., fillings). In one embodiment, the dental compositions of the present invention can be used for at least one of: (i) protecting tooth enamel from dental caries, dental decay, and/or acids; (ii) preventing or treating dentinal hypersensitivity; (iii) improving the cosmetic appearance of teeth; or (iv) any combination thereof. As used herein, "tooth" includes natural and synthetic/artificial teeth.

In one embodiment, the present invention relates to a dental coating or veneer consisting of a layer of a dental composition of the present invention applied to a tooth for protective and/or aesthetic (i.e., cosmetic or tooth whitening) purposes. The dental coating may be applied directly by a trained dental professional or an untrained individual (e.g., the user).

In another embodiment, the dental compositions of the present invention may comprise one or more additives as defined herein, such as an organic additive, an organic dispersant or stabilizing agent, a pigment (e.g., a metallic oxide nanoparticle), a flavor or odor improving agent, or any combination thereof. In another embodiment, the additive can include an anti-caries agent such as sodium fluoride, sodium fluorophosphates, stannous fluoride, or any combination thereof.

In another embodiment, the dental coating of the present invention can possess a quick drying property (e.g., when mixed in a suitable volatile solvent such as ethanol). In another embodiment, the dental coating of the present invention can possess excellent durability and can withstand regular eating (including e.g., acidic food), drinking (e.g., wine), dental floss, and/or brushing for at least one week. In another embodiment, the dental coating of the present invention can withstand regular eating, drinking, and/or brushing for at least 1 month, in another embodiment for at least 2 months, in another embodiment for at least 3 months. As used herein, "regular brushing" constitutes daily brushing with a BRAUN™ electric toothbrush.

In another embodiment, the dental coating can be prepared from a de-colored (e.g., colorless) shellac of the present invention by: (a) dissolving a dental composition of the present invention in a suitable non-toxic, volatile solvent to produce a shellac solution; (b) applying said solution to a tooth; and (c) drying the solution on the tooth. In another embodiment, the non-toxic, volatile solvent can be ethanol. Multiple coats or layers of the dental coatings of the present invention may be applied until the desired result (e.g., whiter color) is achieved. In another embodiment, the shellac/ethanol solution can dry as a clear, transparent coating.

In another embodiment, the dental composition is prepared by dissolving the de-colored (e.g., colorless) shellac of the present invention in ethanol, with or without the presence of organic additives, and applying the shellac/ethanol solution to a tooth. In another embodiment, the shellac/ethanol solution can dry as a clear, transparent or white coating.

Furthermore, dental coatings comprising different pigments (e.g., metallic oxide nanoparticles) or other additives can be mixed or applied in various layers/coats (e.g., with sufficient drying times in between applications (e.g., about 2 minutes) in order to achieve different final colors, shades, luster (e.g., more or less gloss, radiance, or brilliance) and/or textures (e.g., smoother for greater conform) to suit the user (e.g., to match their natural tooth color or to provide a more comfortable, smoother surface). In one embodiment, a coat lacking nanoparticles can be applied subsequent to a previous coat having nanoparticles to produce a smoother outer coating (e.g., for greater comfort).

In another embodiment, all the components of the dental compositions of the present invention are food grade components and/or are non-toxic.

Other Compositions

In another aspect, the present invention relates to other compositions including the de-colored (e.g., colorless) shellac of the present invention. In one embodiment, the composition is for use in coating a food product, and can include one or more preservatives and/or colorants. In another embodiment, the composition is for use as an art material. In another embodiment, the composition is for use as a nail varnish or polish. In another embodiment, the composition is for use as a wood varnish.

The present invention is illustrated in further details by the following non-limiting examples.

EXAMPLE 1

Materials

The colored shellac chosen as raw material was previously bleached and de-waxed by the manufacturer. The following information is from the accompanying safety data sheet, article number 60450, named "shellac": bleached, very light, CAS 9000-59-3; EINECS 232-549-9, color: pale yellow, sold under food grade. Although the product name includes the term "white", the color of the shellac product is in fact pale yellow, as indicated in the data sheet. Other chemicals, unless otherwise mentioned were obtained from a standard chemical supplier such as Sigma-Aldrich.

EXAMPLE 2

Process of De-coloring Shellac

As shown schematically in FIG. 1, methods of de-coloring shellac according to the present invention generally include the following main steps: Dissolution of the colored shellac used as starting material using an alkaline agent; de-colorization/bleaching of the dissolved colored shellac using a bleaching agent; precipitation/recovery of the de-colored shellac using a neutralization agent; recovery, rinsing, and drying of the de-colored shellac. An exemplary process for de-coloring shellac is described below.

In the dissolution step, 10 g of the colored shellac of Example 1 and 4 g of the alkaline agent sodium bicarbonate ($NaHCO_3$), were weighed and transferred to a beaker. Water was added to complete to 100 g, and the contents were heated preferably to about 80° C. while stirring until the reagents completely dissolved (about 15-30 minutes). The color of the solution at this stage was light pink. In the de-colorization/bleaching step, 1 g of the bleaching agent sodium chlorite ($NaClO_2$), was added after cooling the solution to about 30-50° C. by agitation and/or by incubation in ice water. The color of the dissolved shellac mixture at this stage disappeared. In the precipitation step, the shellac solution was neutralized with the neutralization agent acetic acid (e.g., 60 mL of 20% w/w acetic acid/water), and a precipitate of the colorless shellac formed. In the final step, the precipitate was recovered by filtration, washed and dried at room temperature or at about 40° C. The final product was colorless shellac (white) in which the pale yellow color of the starting material was removed.

Experiments comparing various alkaline agents, bleaching agents and neutralization agents are described in Examples 3-7. Experiments describing methods of de-coloring colored shellac, with or without the addition of different additives are described in Examples 8-10 and in FIG. 2. Finally, experiments relating to the preparation and use of different coating product preparations using the de-colored shellac of the present invention are described in Examples 11-13.

EXAMPLE 3

Effect of Various Alkaline Agents

The effect of different types of alkaline agents, namely NaOH, $NaHCO_3$, $Na_2CO_3$, and KOH were compared as described below.

In the dissolution step, 10 g of the colored shellac of Example 1 and 4 g of any one of the alkaline agents mentioned above were weighed and transferred to a beaker. Water was added to complete to 100 g, and the contents were heated preferably to about 80° C. while stirring until the reagents completely dissolved (about 15-30 minutes). In the de-colorization/bleaching step, 1 g of the bleaching agent sodium chlorite ($NaClO_2$), was added after cooling the solution to about 30-50° C. by agitation and/or by incubation in ice water. In the precipitation step, the shellac solution was neutralized with the neutralization agent acetic acid (e.g., 60 mL of 20% w/w acetic acid/water), and a precipitate of the shellac formed. In the final step, the precipitate was recovered by filtration with a glass filter, washed to remove the salt formed during the reaction, and dried at room temperature or at about 40° C.

$NaHCO_3$ was the best performing dissolution agent for the shellac that was used.

EXAMPLE 4

Effect of Various Sodium Bicarbonate Concentrations

The effect of various concentrations of $NaHCO_3$ (see experiment numbers: S48, S49, S50, S46) was then tested (as shown in Table 1), namely from 1 g to 4 g using the method described in Example 2. These experiments revealed, upon inspection of the resulting de-colored shellacs, that 2 g to 4 g of $NaHCO_3$ is the optimal quantity for 10 g of colored shellac in terms of achieved color.

TABLE 1

| Sample # | $NaHCO_3$ (g) | Evaluation of dissolution |
|---|---|---|
| S48 | 1.009 | |
| S49 | 2.023 | |
| S50 | 3.025 | |
| S46 | 4.024 | Optimum |

EXAMPLE 5

Effect of Various Bleaching Agents

The effect of different types of bleaching agents, namely $NaClO_2$ (sodium chlorite), NaClO (sodium hypochlorite), $H_2O_2$ (hydrogen peroxide), HCl (hydrochloric acid), $KMnO_4$ (potassium permanganate) were compared as described below 1 g of any one of the above bleaching agents (in solid form) per 10 g of colored shellac was tested using the method generally described in Example 2. These experiments revealed, upon inspection of the resulting de-colored shellacs, that the best bleaching agent was $NaClO_2$. More particularly, the order of performance was $NaClO_2 >> NaClO > H_2O_2 > HCl > KMnO_4$. Use of $NaClO_2$ as bleaching agent resulted in a white, de-colored shellac product (after drying). Use of $H_2O_2$ as bleaching agent resulted in a product that was not as white as with $NaClO_2$. Use of HCl as bleaching agent resulted in a product that was not as white as with $NaClO_2$, and the physical aspect of the shellac was modified as compared to with $NaClO_2$. Finally, use of $KMnO_4$ resulted in a product having a residual violet color. Results are summarized in Table 2.

TABLE 2

| Sample # | Bleaching agent | Bleaching agent (g) | Evaluation (color remained) |
|---|---|---|---|
| S46 | $NaClO_2$ | 1 | No |
| S4 | NaClO (~5%) | 20 | Yes |
| S5 | HCl (20%) | 5 | Yes |
| S6 | $KMnO_4$ | 1 | Yes |
| S7 | $H_2O_2$ (30%) | 3.5 | Yes |

EXAMPLE 6

Effect of Various Concentrations of Sodium Chlorite

The effect of different concentrations of the bleaching agent $NaClO_2$ was tested from between about 0.5 g to about 1 g using the method generally described in Example 2, and as indicated in Table 3. These experiments revealed that the optimal quantity of $NaClO_2$ was about 1 g, for 10 g of the tested colored shellac.

TABLE 3

| Sample # | NaClO$_2$ (g) | Remark |
|---|---|---|
| S52 | 0.566 | Not enough reagent |
| S46 | 1.002 | Optimum for color removing |
| S8 | 2 | Physical aspect changed |

EXAMPLE 7

Effect of Various Neutralization Agents

The effect of different neutralization agents, namely: HCl, CH$_3$COOH and H$_2$SO$_4$ on the precipitation step was studied using the method generally described in Example 2, and the results are summarized in Table 4. Briefly, the use of acetic acid as neutralization agent was the best overall in terms of appearance, yielding a white, de-colored shellac product. Use of H$_2$SO$_4$ or HCl as neutralization agents yielded a shellac product that was not as good in terms of appearance as with acetic acid when used at the same concentration as the acetic acid. Of note, the "shine remaining" on the de-colored shellac was highest when acetic acid was used (Table 4).

TABLE 4

| Sample # | Neutralization agent | Evaluation of shine remaining* |
|---|---|---|
| S57 | CH$_3$COOH | M |
| S58 | HCl | B |
| S59 | H$_2$SO$_4$ | B |

*E (excellent): >80%; G (good): 75-80%; M (medium): 70-75%; B (bad): <70%.

EXAMPLE 8

De-coloring Shellac in the Presence of Organic Additives

The colorless shellac was produced as generally described in Example 2, but with the exception that 0.5 g of the additive PPG 1000 (polypropylene glycol MW 1000) was added during the dissolution step, as shown schematically in FIG. 1.

EXAMPLE 9

De-coloring Shellac in the Presence of Organic Additives and Nanoparticles

The colorless shellac was produced as described in Example 8, but with the further addition of 0.5 g of TiO$_2$ (United States Pharmacopeial Convention (USP)) nanoparticles during the dissolution step, as shown schematically in FIG. 1.

EXAMPLE 10

De-Coloring Shellac in the Presence of Additives, Nanoparticles and an Anti-Caries Agent The colorless shellac was produced as described in Example 2, but with the addition of 0.5 g of PPG 1000, 0.5 g of TiO$_2$ nanoparticles, and 0.1 g sodium fluoride (NaF) during the dissolution step, as shown schematically in FIG. 1.

EXAMPLE 11

Coating Product Preparations

Method 1: Direct Method

In one embodiment of the present invention, the "direct method" can be used to prepare various coating products comprising de-colored shellac (see FIG. 2, left side), in which additives are added during the initial dissolution step of the colored shellac.

In a 20-mL vial, 2 g of de-colored shellac obtained as generally described in Example 2 was dissolved in 18 g of ethanol (i.e., 10% of de-colored shellac solid in ethanol, w/w) by stirring. A clear film was obtained after drying.

In a 20-mL vial, 2 g of the de-colored shellac obtained as described in Example 9 was dissolved in 18 g of ethanol (i.e., 10% de-colored shellac solid in ethanol, w/w) by stirring, then the mixture was subjected to ultrasound for at least 1 min. A white film was obtained after drying. It was found that the presence of additives increases the resistance of the coating materials as evaluated by ultrasound test.

TABLE 5

| Sample # | Organic additive | TiO$_2$ average size | Evaluation of shine remaining* |
|---|---|---|---|
| S128 | No additive | 15 nm | M |
| S129 | No additive | 25 nm | M |
| S130 | PAA2100 | 15 nm | E |
| S131 | PAA2100 | 25 nm | E |

*E (excellent): >80%; G (good): 75-80%; M (medium): 70-75%; B (bad): <70%.

Method 2: Indirect Method

In another embodiment of the present invention, the "indirect method" can be used to prepare various coating products comprising de-colored shellac (see FIG. 2, right side), in which additives are added during the re-dissolution step of the de-colored shellac.

In a 20-mL vial, 2 g the de-colored shellac obtained as described in Example 2 was dissolved in 18 g of ethanol (i.e., 10% de-colored shellac solid in ethanol, w/w) by stirring. Then, 0.5 g of TiO$_2$ (having an average size of 20 nm) and 0.5 g of organic additive (i.e., polyacrylate MW 2100) was added to the mixture before being subjected to ultrasound for at least 1 min. A white film was obtained after drying. The smaller size particles (15 nm, 25 nm) were better than the bigger size (118 nm) based on the ultrasound evaluation test.

TABLE 6

| Sample # | Organic additive | TiO$_2$ average size | Organic add/total (%) | NP/total (%) | Evaluation of shine remaining* |
|---|---|---|---|---|---|
| S160 | PAA2100 | 15 nm | 0.6 | 0.5 | E |
| S161 | PAA2100 | 25 nm | 0.6 | 0.5 | E |
| S162 | PAA2100 | 118 nm | 0.5 | 0.5 | G |

*E (excellent): >80%; G (good): 75-80%; M (medium): 70-75%; B (bad): <70%.

EXAMPLE 12

Preparation of Natural and Synthetic Teeth for Application of Coating Product

After shaking well by hand and/or using an ultrasound device for re-dispersing the nanoparticles contained in the coating product produced, the coating product was then applied on natural teeth or on polyethylene board (i.e., "synthetic teeth", 1 cm×2 cm). The preparation of natural teeth or of the "synthetic teeth" was carried out as follows:

Preparation of Natural Teeth:
Clean the surface of the tooth using a pumice (optional) and an electric brush for a total of 2 min;
Rinse well with water;
Apply $H_3PO_4$ paste (37%) or citric acid (lemon juice) on over the teeth and wait 15 seconds (optional);
Rinse well with water;
Dry by air/jet of air; and
Apply the coating product using a small brush: 3 to 6 times with 2 min between applications. Wait for about 2 h before testing.

Preparation of "Synthetic Teeth"
A polyethylene board was sanded and cut into 1 cm×2 cm pieces;
Clean in ultrasound bath for 5 min to remove the residues;
Dry at room temperature or in oven at about 50° C.;
Apply using a small brush: 6 times with 2 min between applications; and
Leave for about 2 h before the durability test.

EXAMPLE 13

Method of Evaluating the Coating Product

The durability of the various coating products prepared as described in Example 11 were evaluated as follows:
Method A: on Natural, Human Teeth: The teeth of a dozen individuals were coated with various coating products of the present invention. After 3 applications, the teeth became white and shining. The surface of the coating was very smooth and remaining on the teeth for at least 1 week.
Method B: on "Synthetic Teeth": The 20 mL vial containing the "synthetic tooth" coated with various coating products of the present invention and water was subjected to an ultrasound bath for 1 min×2 times, 2 min×1 time, and finally 5 min×1 time. The synthetic tooth was dried and the shine on the surface of the synthetic tooth was observed after each time. The percentage of shine remaining after each time of ultrasound was observed, estimated and evaluated based on an evaluation code below. The result reported in examples is the % of shine remained after 9 min ultrasound.

Evaluation Code:
E (excellent): >80%
G (good): 75-80%
M (medium): 70-75%
B (bad): <70%

Although the present invention has been described hereinabove by way of specific embodiments thereof, it can be modified, without departing from the spirit and nature of the subject invention as defined in the appended claims.

REFERENCES

Sharma et al., Def Sci J, 33:3, 1983.

The invention claimed is:
1. A method of producing a de-colored shellac composition comprising:
(a) heating and dissolving colored shellac in an aqueous solution comprising an alkaline agent;
(b) contacting said colored shellac in said aqueous solution with a sufficient amount of a chlorite salt to de-color said colored shellac;
(c) precipitating said de-colored shellac by neutralizing the aqueous solution in (b) with an acid; and
(d) recovering said precipitated de-colored shellac from said aqueous solution, thereby de-coloring said colored shellac; and
(e) adding an additive during and/or after (a), (b), (c), and/or (d), wherein said additive is selected from: an organic additive; metallic oxide nanoparticles; an anti-caries agent; a flavor or odor improving agent; and any combination thereof.

2. The method of claim 1, wherein said additive is added during (a).

3. The method of claim 1, wherein said additive added after (d) is added during or after re-dissolution of said de-colored shellac.

4. The method of claim 1, wherein said additive is dispersed by mixing and/or using an ultrasound device.

5. The method of claim 1, wherein said organic additive is an organic dispersant or stabilizing agent selected from: a polymer at low molecular weight, polyacrylate or polyacrylic acid sodium salt (PAA), polyethylene glycol (PEG), polypropylene glycol (PPG), polyepoxysuccinic acid (PES-A) or sodium salt thereof (PES-Na), poly(itaconic) acid, a cellulose derivative, sulfonated carboxylic acid terpolymer, a copolymer of acrylic acid and sulfonated monomers thereof (Co-PAA); and any combination thereof.

6. The method of claim 1, wherein said additive is a small molecule having multifunctional groups selected from: 2-phosphonobutane-1,2,4 tricarboxylic acid; sodium hexametaphosphate (HMP); and any combination thereof.

7. The method of claim 1, wherein said metallic oxide nanoparticles have an average size less than or equal to 75 nm.

8. The method of claim 1, wherein (i) aggregates of said metallic oxide nanoparticles have an average size less than or equal to 100 nm±20 nm; and/or (ii) said metallic oxide nanoparticles have an average size between about 5 nm and 30 nm.

9. The method of claim 1, wherein the metallic oxide in said metallic oxide nanoparticle is an oxide of Ti, Zn, Mg, Si, Al, Ce, Fe, or any combination thereof.

10. The method of claim 9, wherein the metallic oxide in said metallic oxide nanoparticle is selected from: titanium oxide; zinc oxide; magnesium oxide, silicium oxide, aluminum oxide; and any combination thereof.

11. The method of claim 1, wherein said anti-caries agent is selected from: sodium fluoride; sodium fluorophosphate; and stannous fluoride.

12. The method of claim 1, wherein said additive comprises metallic oxide nanoparticles and an organic additive.

13. The method of claim 12, wherein said organic additive is an organic dispersant or stabilizing agent selected from: a polymer at low molecular weight, polyacrylate or polyacrylic acid sodium salt (PAA), polyethylene glycol (PEG), polypropylene glycol (PPG), polyepoxysuccinic acid (PES-A) or sodium salt thereof (PES-Na), poly(itaconic) acid, cellulose derivative, sulfonated carboxylic acid terpolymer, a copolymer of acrylic acid and sulfonated monomers thereof (Co-PAA); and any combination thereof.

14. The method of claim 5, wherein said organic additive is a cellulose derivative and wherein the cellulose derivative carboxymethyl cellulose (CMC).

15. The method of claim 13, wherein said organic additive is a cellulose derivative and wherein the cellulose derivative carboxymethyl cellulose (CMC).

16. The method of claim 6, wherein the 2-phosphonobutane-1,2,4 tricarboxylic acid is DEQUEST™ 7000.

* * * * *